United States Patent [19]
Hursen et al.

[11] 3,944,438
[45] Mar. 16, 1976

[54] GENERATION OF ELECTRICAL POWER

[75] Inventors: Thomas F. Hursen, Monroeville; Steven A. Kolenik, Leechburg; David L. Purdy, Indiana, all of Pa.

[73] Assignee: Arco Medical Products Company, Leechburg, Pa.

[22] Filed: Mar. 11, 1974

[21] Appl. No.: 450,130

Related U.S. Application Data

[60] Division of Ser. No. 171,383, Aug. 12, 1971, Pat. No. 3,818,304, which is a continuation-in-part of Ser. No. 827,187, May 23, 1969, abandoned.

[52] U.S. Cl. ................. 136/202; 136/225; 136/226
[51] Int. Cl.² ......................................... G21H 1/10
[58] Field of Search .................... 136/202, 225, 226

[56] References Cited
UNITED STATES PATENTS

| | | | |
|---|---|---|---|
| 3,055,965 | 9/1962 | Te Velde | 136/226 |
| 3,087,002 | 4/1963 | Henderson et al. | 136/202 |
| 3,282,741 | 11/1966 | Pigford et al. | 136/202 |
| 3,329,532 | 7/1967 | Austin et al. | 136/202 |
| 3,347,711 | 10/1967 | Banks, Jr. et al. | 136/202 |
| 3,357,866 | 12/1967 | Belofsky | 136/202 |
| 3,388,008 | 6/1968 | Campana et al. | 136/202 |
| 3,649,367 | 3/1972 | Purdy | 136/202 |
| 3,728,160 | 4/1973 | Des Champs et al. | 136/202 |

OTHER PUBLICATIONS

Astro Electronics Div., R.C.A., *High Temperature R.T.G. for Space Applications,* Dec. 1964, pp. 9–12, 14, 62–67.

*Primary Examiner*—Maynard R. Wilbur
*Assistant Examiner*—G. E. Montone
*Attorney, Agent, or Firm*—John R. Ewbank

[57] ABSTRACT

A heat-to-electricity converter is disclosed which includes a radioactive heat source and a thermoelectric element of relatively short overall length capable of delivering a low voltage of the order of a few tenths of a volt. Such a thermoelectric element operates at a higher efficiency than longer higher-voltage elements; for example, elements producing 6 volts. In the generation of required power, thermoelectric element drives a solid-state converter which is controlled by input current rather than input voltage and operates efficiently for a high signal-plus-noise to signal ratio of current. The solid-state converter has the voltage gain necessary to deliver the required voltage at the low input of the thermoelectric element.

5 Claims, 25 Drawing Figures

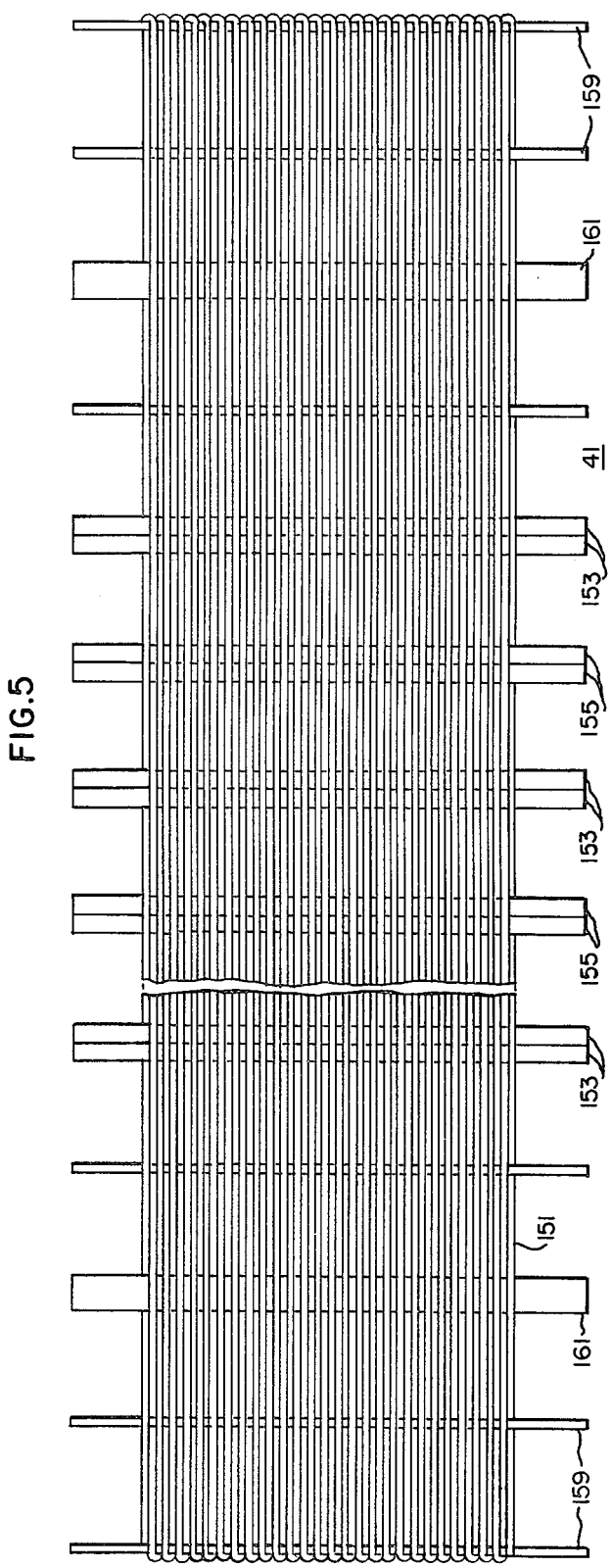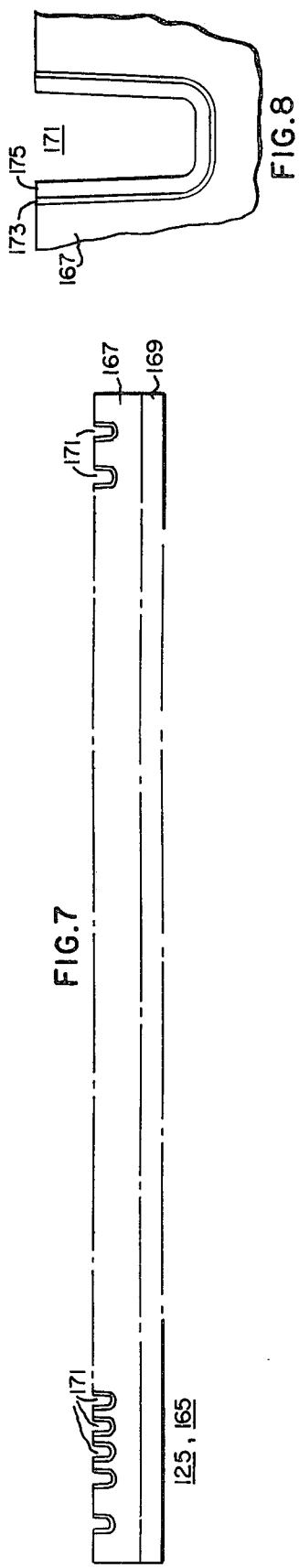

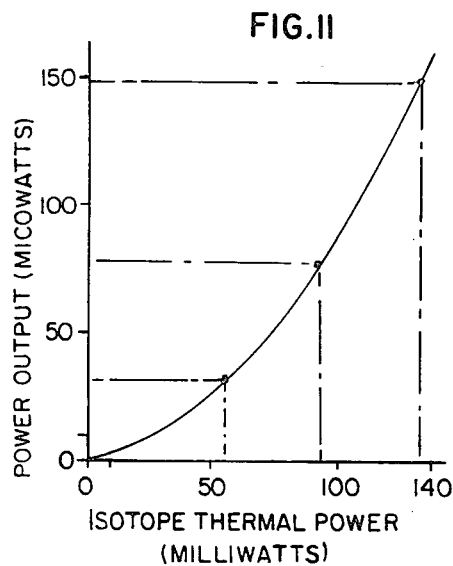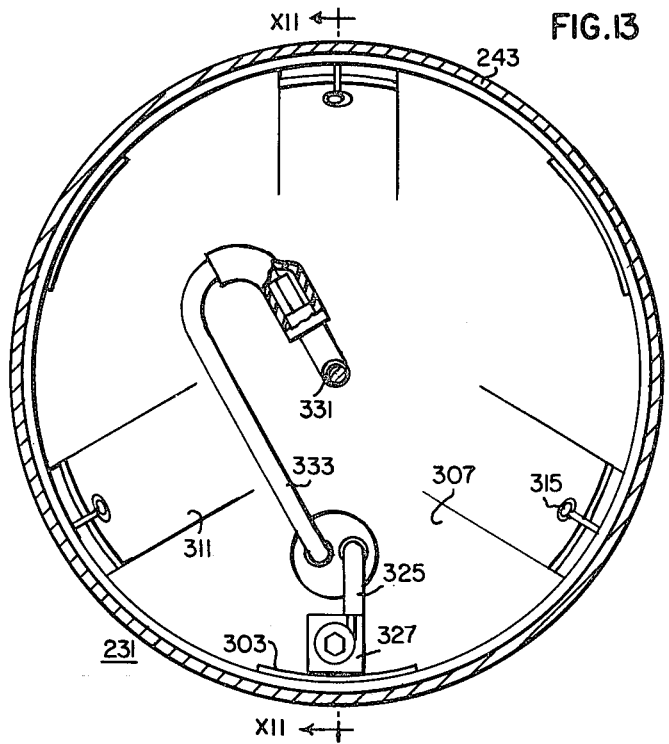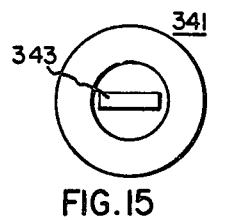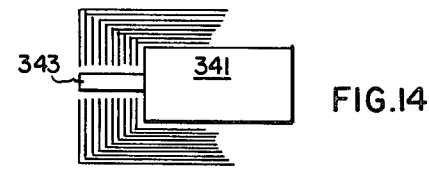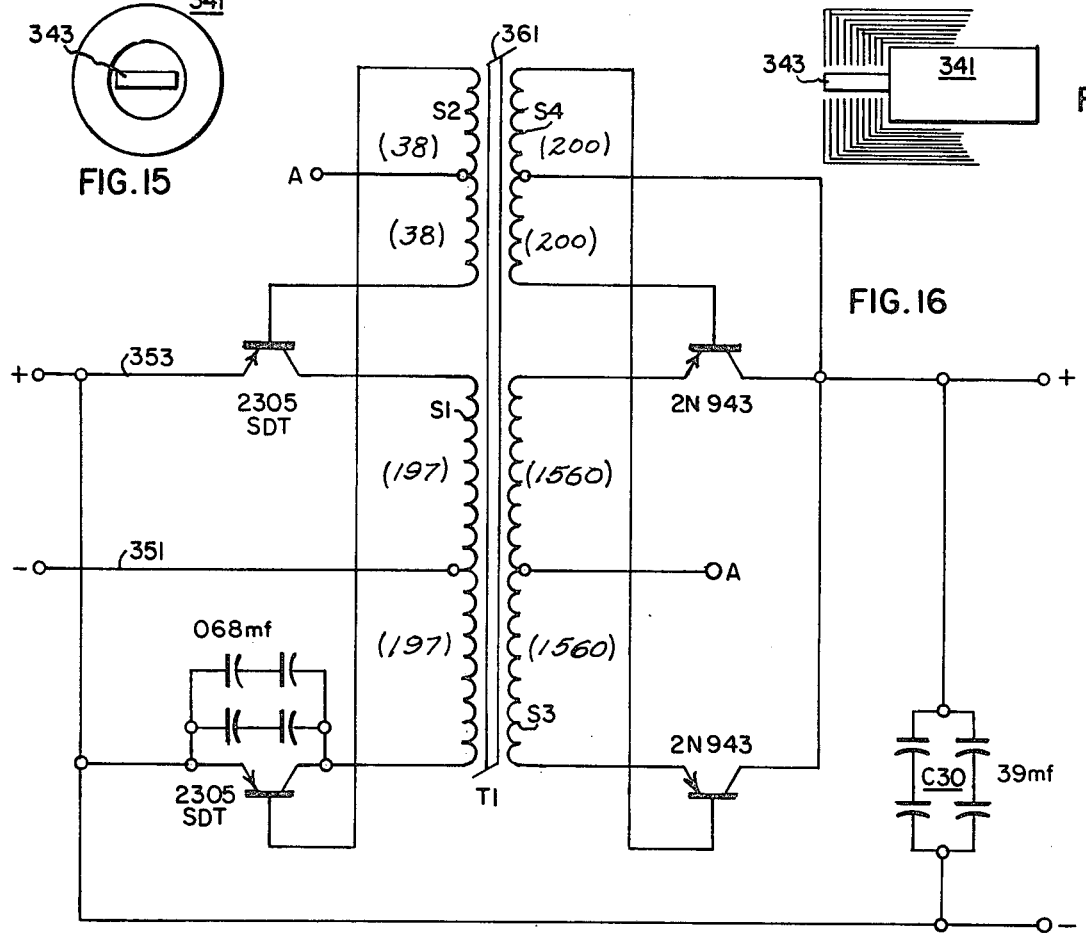

GENERATION OF ELECTRICAL POWER

RELATED APPLICATION

This is a division of Ser. No. 171,383 filed Aug. 12, 1971 now U.S. Pat. No. 3,818,304 which was a continuation of Ser. No. 827,187 filed May 23, 1969, now abandoned.

BACKGROUND OF THE INVENTION

This invention relates to the generations of electrical power and has particular relationship to radioisotope thermoelectric heat-to-electricity converters and to electrical generators which are called RTG's. RTG's include such heat-to-electricity converters and electrical voltage and/or power converters, DC/DC converters, driven by the heat-to-electricity converters. While this invention has general applicability to RTG's of all types, it is peculiarly advantageous and has unique applicability to RTG's whose power output is in the microwatt or milliwatt range. It is an object of this invention to provide an RTG which shall operate at substantially higher efficiency than prior-art RTG's and shall, at the same time, have smaller dimensions and be of substantially lower cost than such prior-art RTG's.

Typically, microwatt and milliwatt RTG's deliver power of between about 100 microwatts and 100 milliwatts. In the interest of concreteness, the RTG of a heart pacer, or pacemaker, will here be discussed. Such a pacer includes an RTG which delivers about 160 to 170 microwatts at about six volts. In accordance with the teachings of the prior-art, such a pacemaker includes a generator having a heat-to-electricity thermoelectric converter which has an output of several volts and has between a thousand and fifteen hundred thermocouples in series. Each thermocouple is long and its component wires are wound in a spiral or otherwise disposed in layers about the heat source. An electrical converter is driven by this heat-to-electricity converter. While this generator performs satisfactorily, it has a very low efficiency and is of comparatively large dimensions, particularly for insertion in the body of a person. Typically, this pacemaker is of rectangular form, having dimensions of 2.5 × 2 × 1.3 inches. This pacemaker has an efficiency of only 0.065%.

It is accordingly an object of this invention to overcome the above described disadvantages of the prior-art and to provide a heat-to-electricity thermoelectric converter of substantially higher efficiency than prior-art such converters, and also to provide an RTG including such a heat-to-electricity converter of relatively higher efficiency and smaller dimensions than prior-art RTG's.

SUMMARY OF THE INVENTION

This invention arises from a radical departure from prior-art thinking that to maintain a substantial temperature difference between the hot and cold junctions of a thermoelectric element, the length of the wire components or couples of the element should be high. It has been realized in arriving at this invention, that, in fact, the length of these components has substantially no effect on the power output of a thermoelectric element.

The power output of a thermoelectric element is given by the equation:

$$P = \frac{E^2}{4R} \tag{1}$$

where:
P is the power output,
E is the open circuit voltage of the element,
R is the resistance of the element.

$$R = \frac{\rho l}{A} \tag{2}$$

where:
P is the resistivity of the wire components of the element,
l is the length of the wire components,
A is the cross-sectional area of the wire components.
Then:

$$P = \frac{E^2 A}{4 \rho l} \tag{3}$$

That is:
P varies inversely as the length.
The heat loss by longitudinal heat flow through a thermoelectric element is given by:

$$H = \frac{KA \Delta T}{l} \tag{4}$$

where:
H is the heat loss,
K is the conductivity of the wire components,
$\Delta T$ is the difference between the hot and cold junction.

$$\frac{P}{H} = \frac{E^2}{4K\rho \Delta T} = \frac{\alpha^2 \Delta T}{4K\rho} \tag{5}$$

where $\alpha$ is the Seebeck coefficient

This ratio is independent of the length. No appreciable advantage is then achieved by use of thermoelectric elements having long wire components as taught by the prior-art.

The heat flow H of equation (5) is the heat conducted through the thermoelectric wires longitudinal of the element. Where the elements are wound in spirals of otherwise layered, this is not the only conductive heat loss. Heat also flows laterally through the elements from layer to layer.

The layering in prior-art heat-to-electricity converters results not alone from the prior-art view that the wire components must be long. it is also a prior-art teaching that the overall voltage output of the thermoelectric converter should be high. This output is given for N thermocouples in series, by:

$$V = NE \Delta T \tag{6}$$

where: V is the total voltage. Where V is to be 6 volts, as many as 1,200 elements in series are required. So high a number of elements of substantial length must be closely layered and the lateral heat flowing through the layers is high.

In arriving at this invention, it has been realized that advantageously the voltage output of the heat-to-electricity converter may be small and may be raised by a solid-state electrical converter. Such a converter differs from an electronic vacuum-tube converter in that it operates by current rather than voltage control. To control a solid-state converter, maximum signal-plus-noise-to-noise ratio of the current, rather than of the voltage, is desirable. This desideratum is achieved by short thermoelectric elements.

In accordance with this invention, a heat-to-electricity converter is provided which includes a heat source and a thermoelectric element in the form of a single strip having a hot-junction in heat-interchange-or-exchange relationship with the source and a cold junction in heat-interchange-or-exchange relationship with a heat sink. The shortners of this element does not affect its power output.

Further, in accordance with this invention, the number of thermoelectric couples in the thermoelectric element is minimized and the voltage output of the element is relatively low, of the order of a few tenths of a volt. To achieve the desired voltage, a generator is provided which includes the above described heat-to-electricity converter and a solid-state electrical converter which is driven from the heat-to-electricity converter and is capable of delivering the desired voltage.

An important advantage of the heat-to-electricity converter, according to this invention, is that the thermoelectric element is not layered or wound in a spiral and there is no heat loss by thermal conduction laterally of the element. Specifically, the heat-to-electricity converter is enclosed in an evacuated container whose outer casing or wall serves as a heat sink. Radiation of heat between the hot junction and the wall is suppressed by a heat radiation shield which is composed of sheets of heat reflecting material. In the practice of this invention, the heat source is of radioactive material which emits gamma rays and the heat shield is composed of sheets of tantalum or of a tantalum alloy. The tantalum not only has marked heat-radiation shielding advantages, but also serves as a shield for the gamma rays.

The thermoelectric strip is disposed in a cavity in the radiation shield. It is to be realized that this invention may also be practiced with a thermoelectric strip consisting of a few layers well spaced throughout the shield between the source and the wall. In this case also, lateral heat flow is suppressed and the heat loss, by conduction through the layers, is minimized.

The generator, according to this invention, is substantially smaller than analogous prior-art apparatus for analogous purposes because of the considerably smaller length of the thermoelectric elements and considerably smaller number of turns. A typical generator for a pacemaker is cylindrical, having a diameter of 1.5 inches and a height of 1.5 inches. The efficiency of the generator, according to this invention, is substantially higher than for prior-art generators and the mass of radioactive material demanded for the same life is smaller for this invention than for prior-art generators. A preliminary unit of the above described smaller pacemaker has an efficiency of 0.085%.

In general, the output of a prior-art heat-to-electricity converter is 170 microwatts at 6 volts. This prior-art generator requires a heat source of Pu 238, capable of delivering 238 milliwatts of heat power. The efficiency of the heat-to-electricity converter is about 0.070%. This prior-art converter drives an electrical converter, having an efficiency of about 35%, which supplies the load.

Generally, heat-to-electricity converter, in accordance with this invention, delivers about 0.3 to 0.5 volts, which is stepped up to 8 volts in a solid-state converter. The heat-to-electricity converter has an efficiency of about 0.12% and it is anticipated will ultimately have an efficiency of 0.24%. The solid-state converter has a substantially higher efficiency than 35%. The quantity of Pu 238 is such as to supply only about 140 milliwatts of heat power; it is anticipated that ultimately only 70 milliwatts will be required. The improvement in efficiency of the heat-to-electricity converter is achieved by eliminating the lateral heat flow through the thermoelectric strip or tape. In addition, the solid-state converter is simplified. The quantity of off-gassing within the evacuated container is critical to the life of the apparatus. The primary source of the off-gassing is the thermoelectric strip or tape. In the practice of this invention, the volume of this material is typically reduced to less than 1% of the volume in prior-art apparatus.

BRIEF DESCRIPTION OF THE DRAWINGS

For a better understanding of this invention, both as to its organization and as to its method of operation, together with additional objects and advantages thereof, reference is made to the following descriptions, taken in connection with the accompanying drawings; in which:

FIG. 5 is a plan view of the thermoelectric element of the generator shown in FIG. 1;

FIG. 6 is a view in side elevation of this element;

FIG. 7 is a view in side elevation of a hot or cold shoe of the thermoelectric element of the generator shown in FIG. 1;

FIG. 8 is an enlarged view of the portion of FIG. 7 shown in circle VIII;

FIG. 11 is a graph of the power output as a function of heat power input for a generator as shown in FIGS. 1 through 10;

FIG. 13 is a view in transverse section taken along line XIII—XIII of FIG. 12;

FIG. 14 is a view generally diagrammatic showing, in longitudinal section, a heat-to-electricity converter constituting another embodiment of this invention;

FIG. 15 is a view generally diagrammatic showing the converter of FIG. 14 in end elevation, with respect to FIG. 14;

FIG. 16 is a schematic showing the component magnitudes, identifications, and connections of a solid-state electrical converter which is included in a generator with heat-to-electricity converters as shown in FIGS. 3, 12, or 14.

FIGS. 10 and 16 are disclosed for the purpose of aiding those skilled in the art in practicing this invention and not with any intention of, in any way, limiting this invention.

DESCRIPTION OF EMBODIMENTS

Figure 2:
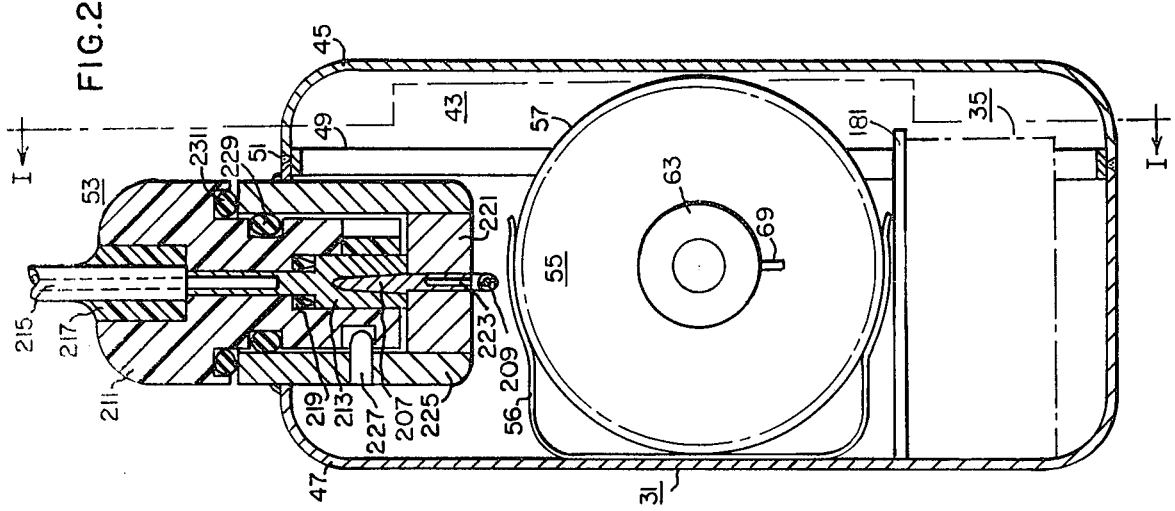
FIG. 2 is a view in section taken along line II—II of FIG. 1.

FIGS. 1 through 10 show a generator 31, including a heat-to-electricity converter 33 and a solid-state electrical converter 35. The converter 33 (FIGS. 3 and 4) includes a radioisotope heat source 39 and a thermoelectric element 41 (FIGS. 5 through 8).

The generator 31 includes a flat generally circularly cylindrical evacuated casing or container 43. The top 45 is welded vacuum tight to the body 47 of the casing typically by election-beam welding. A back-up ring 49 is provided behind the weld 51. Terminal 53 is sealed vacuum tight through the periphery of the body 47.

The heat-to-electricity converter 33 is encased in a cylindrical container 55 mounted between the jaws of a C-shaped spring bracket 56 secured to the body 47. The container 55 is formed of a cylindrical shell 57 to which bases 59 and 61 are welded vacuum tight. The base 61 has a hollow stem 63. A ceramic feed-through terminal 66 is sealed vacuum tight through the base 61 and extends into a potting compound 67 within the hollow terminal 65. An output wire 69, connected to an output tab 71 within the container 55, extends through an insulating section 73 of the stem 63.

The containers 43 and 55 and the wire 69 are typically composed of titanium. The potting compound 67 is a silicone compound.

The heat source 39 is a capsule disposed generally centrally within the container 55. This capsule 39 is generally cylindrical and includes a central cylindrical bar 79 of radioactive material, typically Pu 238, enclosed in cylindrical concentric shells 81, 83, 85. The inner shell 81 is composed typically of tantalum 10% tungsten alloy to absorb gamma rays and the cylinder 79 is sealed in this shell by a plug 87 of this Ta 10% W alloy. The central shell 83 is composed of HASTELLOY-C alloy and the shell 81 is sealed in the shell 83 by a plug 89 of HASTELLOY-C alloy. The outer shell 85 is composed of titanium 0.2% palladium alloy and is sealed by a plug 91 of the same alloy. The capsule 39 is enclosed in a shell 93 and is disposed between discs 95 and 97.

Figure 4:
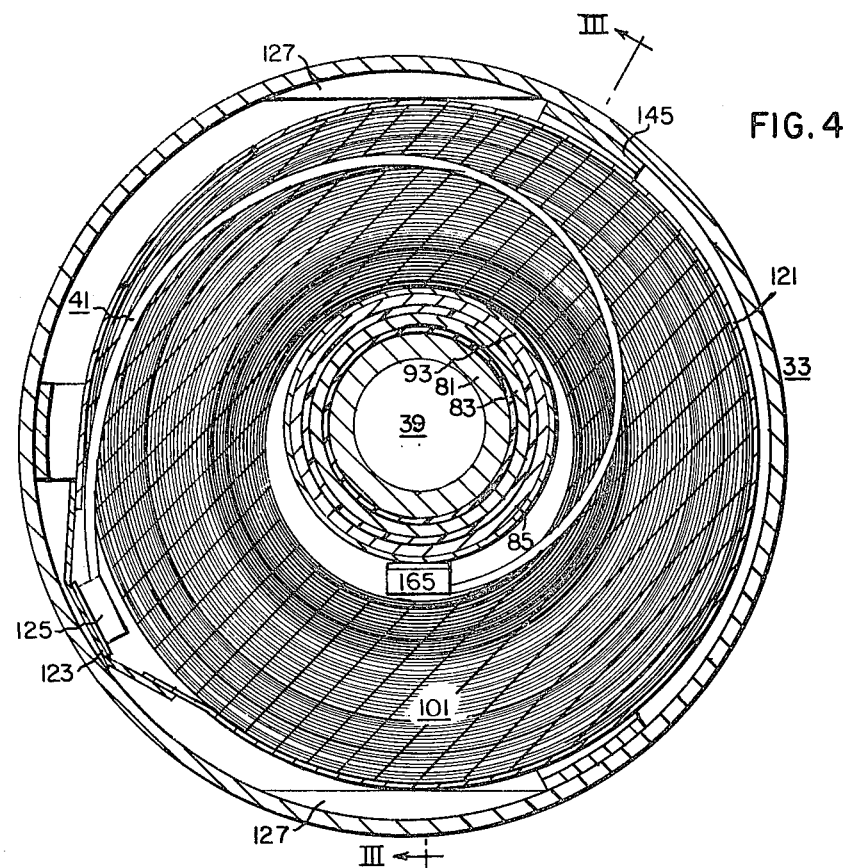
FIG. 4 is a view in section taken along line IV—IV of FIG. 3.
Figure 4A:
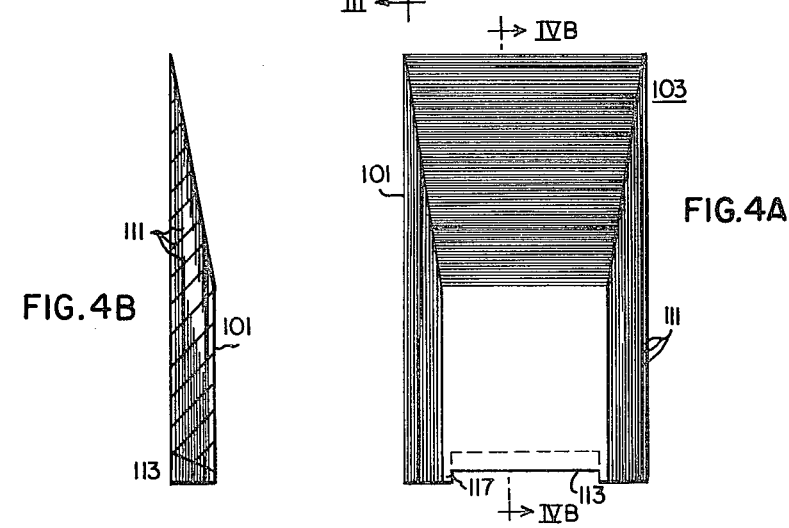
FIG. 4A is a plan view showing a stack of sheets of heat-radiation shielding foils prepared for use in the apparatus shown in FIG. 4.
Figure 4B:
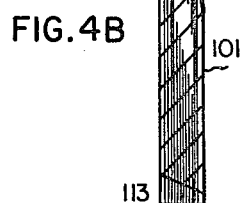
FIG. 4B is a view in section taken along line IV-B—IVB of FIG. 4A.
Figure 4C:
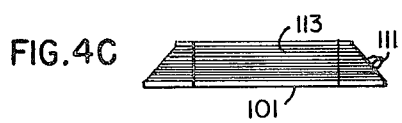
FIG. 4C is a view in end elevation of the foils shown in FIG. 4A.
Figure 4D:
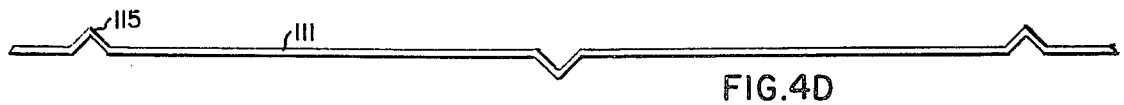
FIG. 4D is a view in end elevation of a foil developed and showing the manner in which it is dimpled.

The fuel capsule 39 constitutes a heat source for the thermoelectric element 41 and the wall 57 constitutes a heat sink. Heat radiated from the source to the sink is suppressed by a heat shield 101 which envelops the capsule 39. The shield 101 is formed of layers of tantalum foil and includes a central portion 103, formed of coaxial foil cylinders, and end portions 105 and 107 of generally frusto-conical form. The central portion 103 is formed of sheets 111 of progressively increasing length as shown in FIGS. 4A, 4B, 4C. The sheets 111 have slots 113 at the ends which increase in width progressively as shown in FIGS. 4A and 4B. Grooves or dimples 115 extend across the sheets as shown in FIG. 4D. The grooves 115 extend parallel to the slots in approximately half the sheets and perpendicular to the grooves in the others. Typically there may be 99 sheets, 50 grooved parallel to the slots 113 and 49 grooved perpendicular to the slot 113.

Each sheet 111 is formed into a cylinder having its axis parallel to the long dimension of the slot 113. Some cylinders (every fourth or fifth) of the ear 117 bounding the slots are welded to the opposite edge of the sheet engaging the ears.

The cylinders are stacked in the container 55 with the grooves 115 of successive cylinders at right angles to each other; that is, the grooves 115 of the odd cylinders, counting from the center, are along the lengths of the cylinders and the grooves 115 of the even cylinders are circumferential. The slots 113 of the stack form a generally spiral slot through the center of the stack. The thermoelectric element 41 extends through this slot. Since the slots 113 are displaced to form the spiral slot, sheet material is interposed between the capsule and the wall 57. A strap or strip 121 is wrapped around the stack 101. The strap 121 is bent in generally trapezoidal cross-sectional form away from the stack 101 near one end 123 and is at this end joined to its opposite end. The thermoelectric element 41 passes out of the spiral slot into the space between the trapezoidal section 123 and the stack 101 and the cold shoe 125 of the element 41 is brazed to the center part of the trapezoidal section 123. The strap 121 is held by diametral springs 127.

The central stack 101 forms surfaces of generally truncated conical form at both ends and these surfaces are engaged by, and mate with, the coextensive truncated conical surfaces of the portions 105 and 107.

Each truncated conical portion 105 and 107 is formed of a plurality of discs 131 which are advantageously composed of tantalum. The discs 131 are of progressively smaller diameter from the base of the truncated cone to the top. The discs 131 may be dimpled similarly to the sheets 111; the dimples in alternate discs may be radial and the dimples in the intervening sheets may be circumferential so as to minimize heat flow by conduction through the discs 131.

The truncated conical portions 105 and 107 are mounted on platforms 133 and 135 respectively of a cagelike bracket 137. This bracket includes cooperative parts 139 and 141. One part 139 may be regarded as holding the top-end portion 105; tongues 143 extend from its platform 133. The other part may be regarded as holding this bottom-end portion 107; long arms 145 extend from its platform 135. The tongues 143 and the arms 145 are joined by welding at the top end. Each of the portions 105 and 107 includes a cover 147 and 149 which engages the plates 95 and 97 respectively. These plates are composed of CERALLOY 400, a getter alloy.

The thermoelectric element 41 is a tape composed of a woof 151 of yarn or glass or quartz or other insulating material. In the longitudinally central part of the tape, the warp is composed of alternate pairs 153 and 155 of wires of opposite polarity thermoelectric material. Typically, the wires 153 may be TOPHEL Special alloy and the wires 155 can be of CUPRON Special alloy. Near each end, the tape has a warp thread 159 of glass or quartz fibers in the like and at least one stiffening warp wire 161 of titanium aluminum vanadium alloy. This wire 166 has a diameter of the wires 153, 155. The woof threads are looped, insulating the pairs of wires 153 and 155 from each other. There are typically approximately 52 pairs each of wires 153 and 155 so that 52 thermocouples are formed.

The thermoelectric element also includes the cold shoe 125 and a hot shoe 165. Each shoe includes a ceramic strip 167 (FIGS. 7 and 8) preferably of high-purity alumina, $Al_2O_3$, having a thin strip of copper 169 with a lip at its end brazed to its base. This brazing is effected by coating the base with a thin coating of titanium, placing a foil on the coating, engaging the foil with the copper strip 169, and heating the joint to the eutectic temperature of copper-titanium. (See Purdy, et. al., Ser. No. 624,916, filed Mar. 21, 1967, for Method of Metals Joining and Article Produced by Such Method.) The ceramic strip 167 has grooves 171 along its length (typically 52 in number). Each groove 171 has a coating 173 (0.0002 inches typically) of titanium. On the titanium, there is a deposit 175 constituting six layers alternately of copper and silver. Typically, a layer about 0.00005 inch thick of copper is deposited, a layer 0.00016 inch thick of silver is deposited on the copper, another layer 0.00005 inch thick is deposited on the silver, and so on until a deposit about 0.0013 inch thick is produced. A large number of grooves containing electrically conducting material, each insulated from the others, is thus produced. The ends of two successive pairs of wires 153 and 155 are brazed to the deposits 175 at each end of the tape. Four wires are brazed in each groove 171, two of one thermoelectric polarity, and two of the opposite polarity. Hot junctions are thus formed in the hot shoe 165 and cold junctions in the cold shoe.

Figure 1:
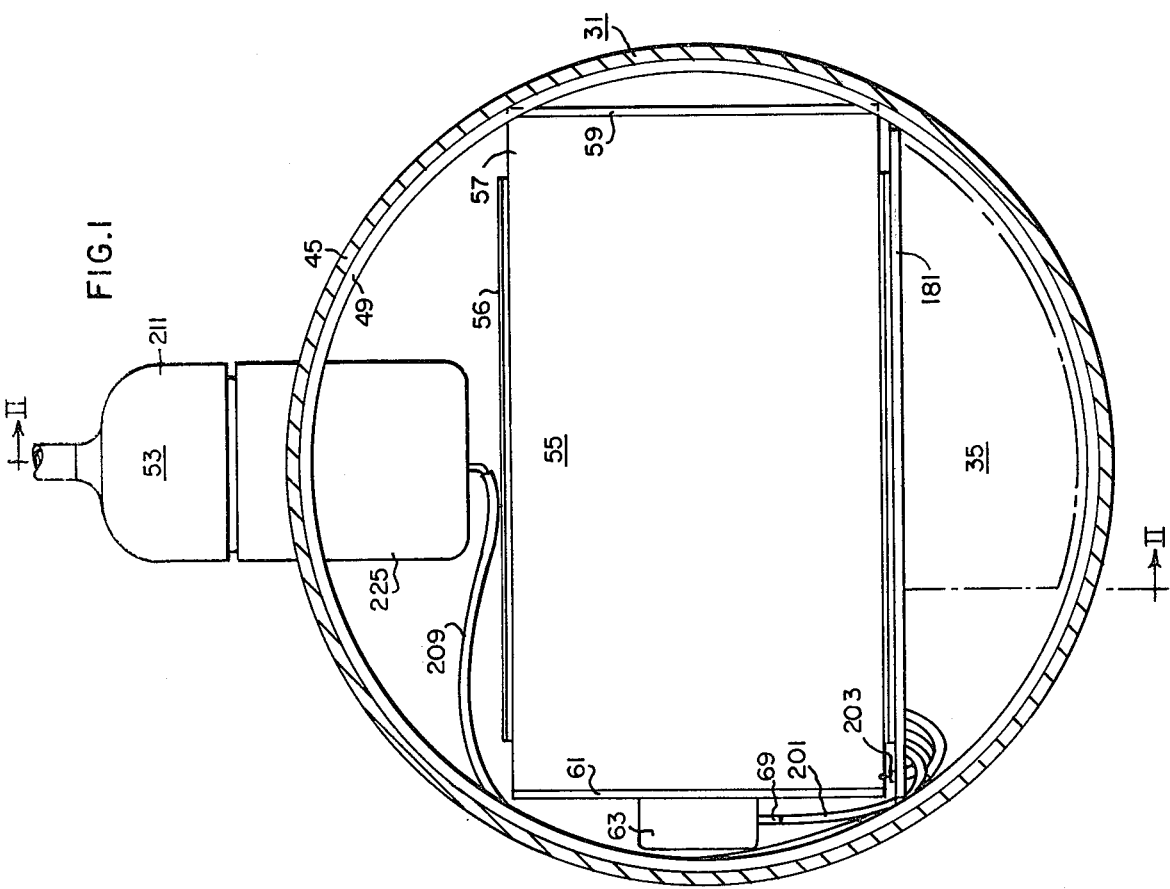
FIG. 1 is a view, with the wall parts in transverse section, of a generator constituting an embodiment of this invention.
Figure 3:
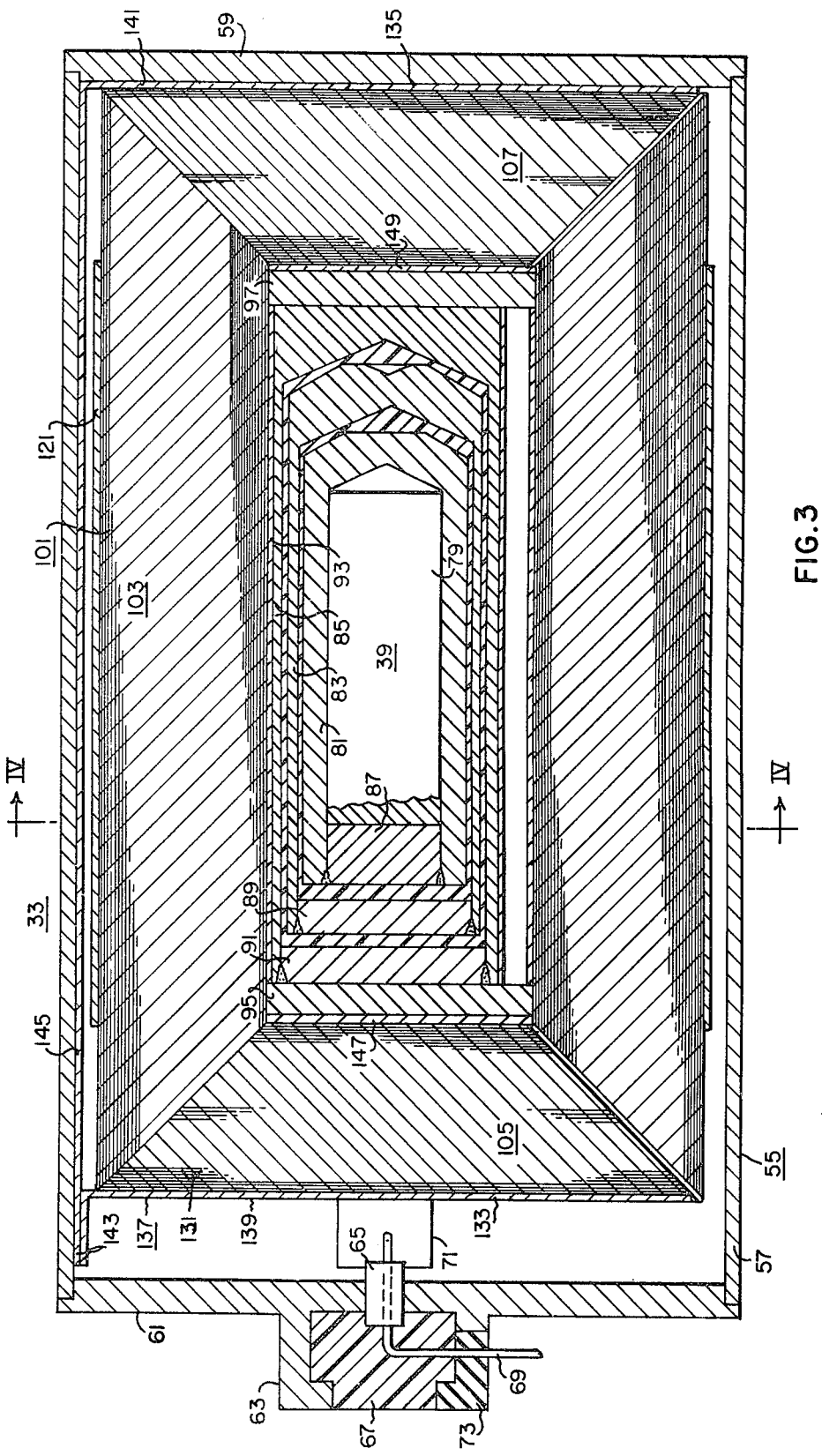
FIG. 3 is a view in section, taken along line III—III of FIG. 4, of the heat-to-electricity converter of FIG. 1.

The thermocouples 153 – 155 are connected in series double redundancy; that is, there are two thermocouples in parallel in each branch of the series network. Typically, there are 52 such pairs of thermocouples in series. The cold junction of the last thermocouple of the network is the "hot" output terminal. This terminal is connected to conductor 69 (FIG. 1) which is sealed through the ceramic feed through bushing 65 (FIG. 1). The cooperative terminal is grounded, the wall 57 of container 55 serves as ground. The output voltage of the thermoelectric element is typically about 0.3 to 0.6 volts.

In making a heat-to-electricity converter 33, the strip or strap 169 for the hot shoe 165 is brazed to the shell 93 of the fuel capsule 39. The foil cylinders 103 are then wrapped about the capsule 39 with the tape 41 in the grooves 113. The strap 169 of the cold shoe 125 is then brazed to the strap 121, which is wrapped about the cylinders 103 and welded at its ends. The cold junction of one terminal of the series network of thermocouples is grounded to casing 55 and the cold junction of the opposite thermocouple is connected to wire 69. The parts 105 and 107 are then mated with the frusto-conical surfaces of the section 103, and the lips 143 and strips 145 joined. The assembly is then placed in container 55 and the container evacuated and sealed.

The electrical converter 35 is mounted on a printed circuit board 181. This converter includes a network 183 (FIGS. 9 and 10) for deriving from the low voltage of the thermocouple a substantially higher DC voltage. This network 183 includes a transformer T having windings N1, N2, and N3, and a SUPERMALLOY alloy core 184. Such a transformer has a substantially rectangular hysteresis loop. Windings N1 and N2 are connected to form a midtap 185. The hot terminal 187 of the thermoelectric element 41, which is electrically negative, is connected to the midtap 185. The network 183 includes transistors Q4 and Q5. The emitters of Q4 and Q5 are connected together to the positive grounded terminal 180 of the thermoelectric element. The collectors of Q4 and Q5 are connected respectively to the remaining terminals of the windings N1 and N2. Each base of transistors Q4 and Q5 is connected to the collector of the other transistor Q5 or Q4. The output current from the thermoelectric element 41 flows directly through the windings N1 or N2 and the collector and emitter of transistor Q5 or Q4 in opposite directions.

The transistors Q4 and Q5 conduct alternately, each producing abrupt saturation of the core 184 which, in turn, causes the other transistor Q5 or Q4 to conduct. The current flow through the windings N1 and N2 is thus abruptly reversed. N3 has about ten times as many turns as N1 or N2 and, on each reversal, a high voltage pulse (typically about 3 volts) is produced at its terminals. Winding N3 is connected to a voltage doubler, including capacitors C4 and C5 and diodes D1 and D2. Typically, the doubler produces about 6 volts DC.

The DC voltage supplies a pulser 101, including transistors Q1, Q2, and Q3. Q1 and Q2 operate as a free-running multivibrator. When voltage from the doubler is first applied, the base of Q1 is connected to the positive terminal through R4 and R5 and Q2 conducts. A negative pulse is impressed on the base of Q1 through capacitor C1 and resistors R2 and R1. Q1 then conducts through R3 and R8, causing Q3 to transmit a pulse. The conduction of Q1 impresses a negative bias on Q2 through C2, stopping its conduction. Conduction of Q1 is stopped by discharge of C1 through R1; Q3 follows Q1 and stops conducting. C2 then charges slowly through the high resistor R5, ultimately applying a positive bias to the base of Q2 and repeating the process.

The pulses through Q3 are impressed in the load through capacitor C3. This capacitor is necessary where the load is a human or animal heart to prevent DC from flowing to the heart. Zener diode VR1 is connected across C3 through R7. The purpose of VR1 is to prevent the flow of high voltage when fibrillation occurs and a high voltage is impressed to defibrillate.

Figure 10:
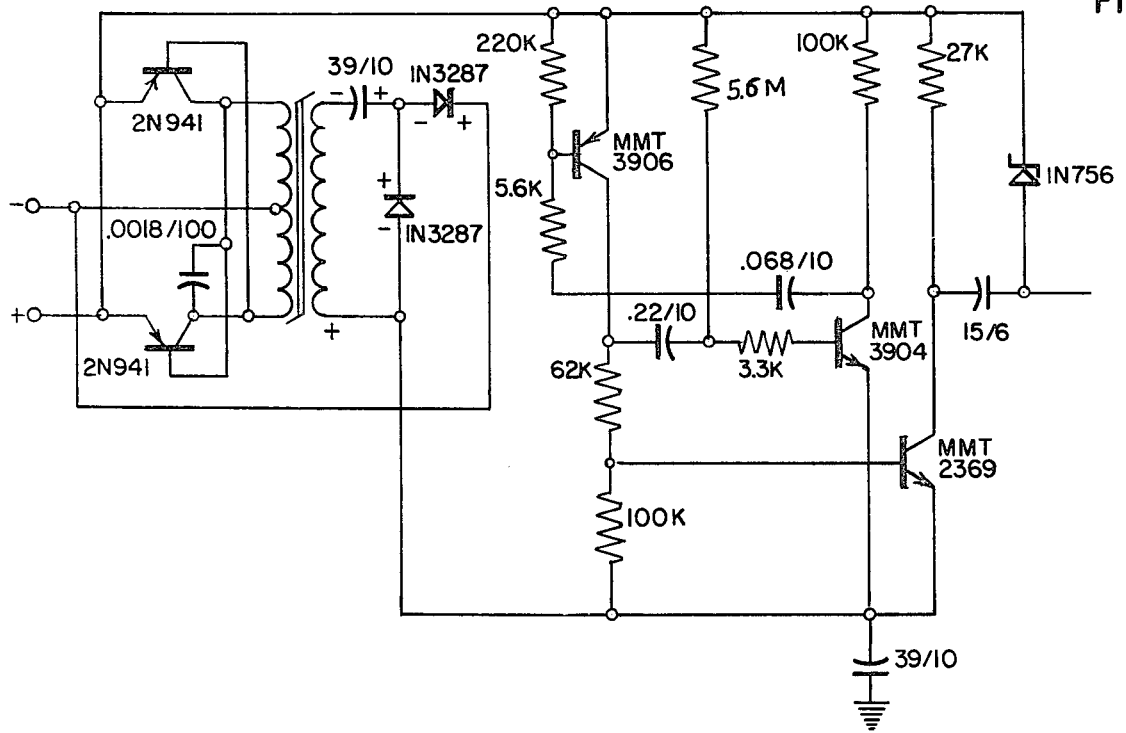
FIG. 10 is a schematic similar to FIG. 9, but showing the component magnitudes and identifications of a converter used in the practice of this invention which was found to operate satisfactorily.

In FIG. 10, the magnitudes including a slant line near a capacitor, for example, 0.068/10 V., gives the capacity in microfarads on the left and the voltage at which the capacitor is rated on the right. Thus, 0.068/10 V. means an 0.068 microfarad capacitor rated at 10 V.

The output conductor 69 from the heat-to-electricity converter 33 is connected to the input terminal 187 of the network 183 through a cable 201. The output ground terminal of the converter 35 is grounded to the casing 57 through another cable 203. The output terminal 205 of the converter 35 is connected to the jack 207 of output terminal connector 53 through a cable 209.

The output terminal converter 53 includes a shoulder-like cylindrical body, member 211 of DELRIN composition, or the like, which serves as an insulator. A receptacle 213, typically of titanium, extends through the center of the body member 211 and is connected to an output conductor 215. The jack 207 engages a tapered hole in the receptacle 213 in good conducting relationship. The member 211 has a cavity in which the conductor 215 is sealed in a SILICONE potting compound 217, or the like. The receptacle 213 has a shoulder and an O-ring 219 is compressed between the body member 211 and the shoulder. The jack 207 is held firmly by cylindrical plug 221, typically of titanium, which firmly engages the stem 223 of the jack 207. A sleeve, typically of titanium, encircles the plug 221 and member 211. A key 227 is provided for locking the sleeve 225 and the body member 211. An O-ring 229 is compressed radially between the sleeve 225 and the peripheral boundary of a groove in the body member 211. Another O-ring 231 is compressed axially between the end of the sleeve 225 and the boundary of an axial groove in the body member 211. The wall 47 is welded to the sleeve 225.

Figure 9:
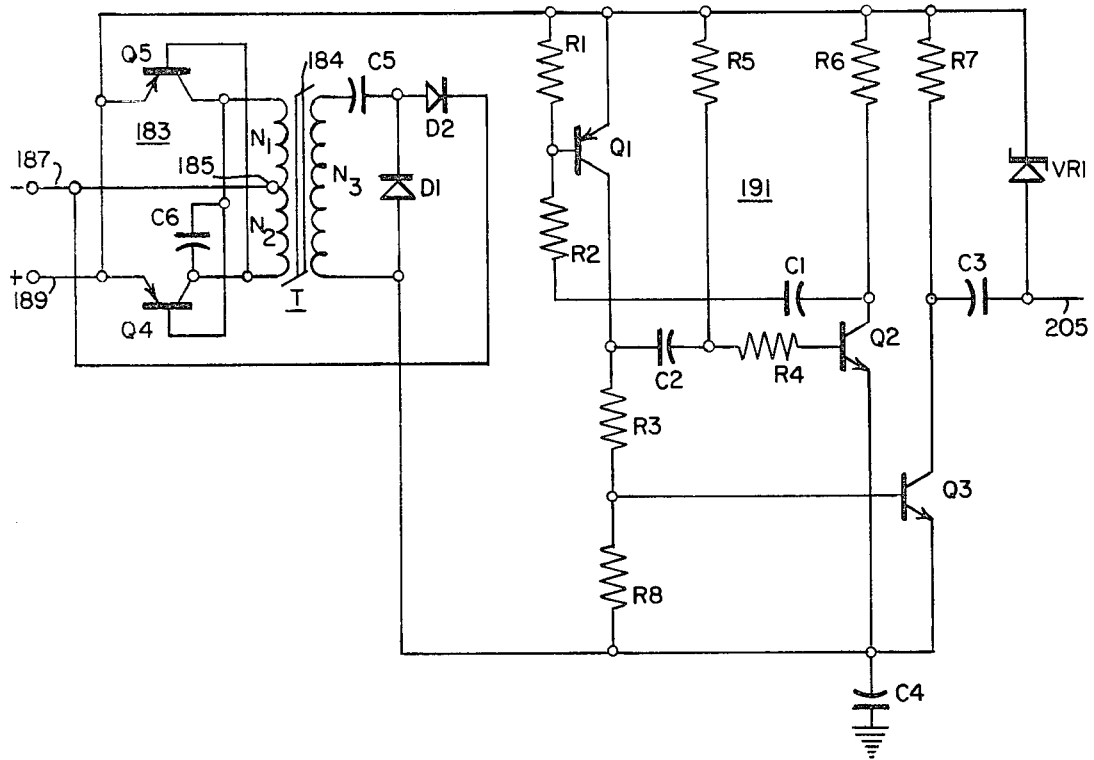
FIG. 9 is a schematic of the electrical solid-state converter of the generator shown in FIG. 1.

In use, the generator shown in FIGS. 9 and 10 has operated with, and produced signals, having the following characteristics:

| | |
|---|---|
| Open circuit voltage of heat-to-electricity converter | .6 Volts |
| Input voltage to converter 35 at terminal 187 | .352 Volts |
| Current input to converter 35 through terminal 187 | 467 microamperes |
| Power input to converter 35 | 164 microwatts |
| Resistance of thermoelectric element 41 | 530 ohms |
| Output pulse rate at terminal 205 | 71 pulses per minute |
| Duration of pulse | 1.56 milliseconds |
| Leading edge of pulse | 6 milliamperes |
| Trailing edge of pulse | 4 milliampers |

FIG. 11 is a graph of the actual power output as a function of the actual heat-power input for a generator as shown in FIGS. 1 through 10. The heat capsule 39, in this case, included Am 141 instead of Pu 238 as the fuel. In FIG. 11, electrical power output in microwatts is plotted vertically and heat power input in milliwatts is plotted horizontally. The efficiency is given by dividing the output by the input. FIG. 11 shows that for low input and output, the efficiency is low (for example, 0.05% at 57 milliwatts input and 30 microwatts output) but that the efficiency increases as the input and output increase. The input for 160 microwatts output is 137 milliwatts and the efficiency is 0.12%.

Figure 12:
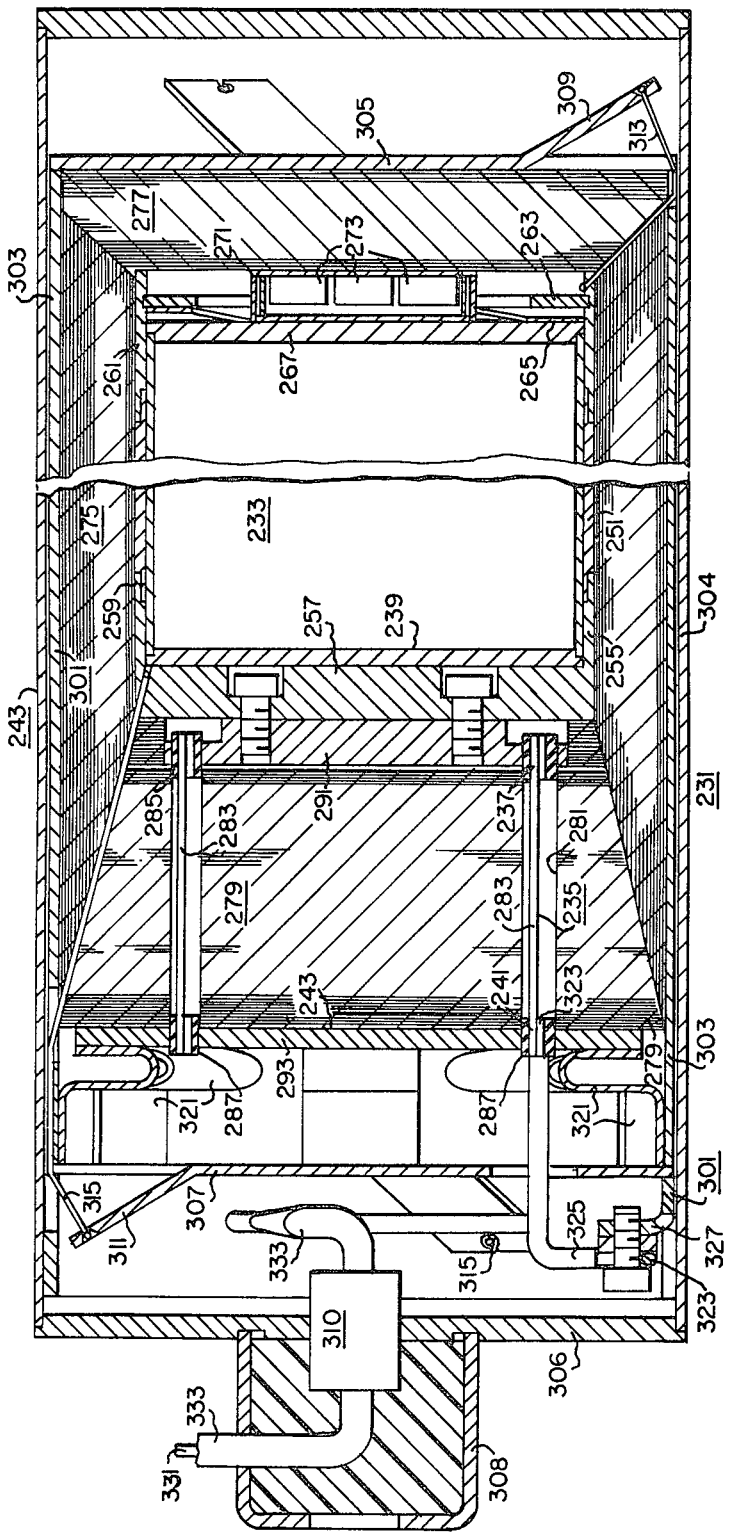
FIG. 12 is a view in longitudinal section taken along line XII—XII of FIG. 13, showing a heat-to-electricity converter which constitutes another embodiment of this invention.

FIGS. 12 and 13 show a heat-to-electricity converter 231, including a heat capsule 233 and an annular thermoelectric element 235 having its hot junction 237 in heat interchange relationship with one end or base 239 of the capsule 233 and its cold junction 241 in heat transfer relationship with the wall 243 of the converter.

The capsule 233 includes a plurality of closed cylinders (not shown) similar to the capsule 39 of the embodiment shown in FIGS. 1 through 10. But the fuel (not shown) is preferably in the form of pellets concentrated near the base 239 of the capsule 233 to which the hot junction 237 is connected. The capsule 233 is enclosed in a cage-like cylindrical enclosure, including strips 251 in the form of cylindrical arcs extending along the wall 253 of the capsule. The strips mate at one end with a member 255, including a disc 257 from which mating fingers 259 extend. At the other end, the strips 251 mate with short strips 261 which carries an annular plate 263. A spring washer 265 resiliently engages the base 267 and the annulus 263. To the base 267, a cylindrical box 271 is centrally secured. In the box 271, there are cylindrical pellets 273 of gettering material.

The capsule 233 is enclosed in heat-radiation shielding foil similarly to the capsule 39. The foil may be composed of titanium, zirconium, or MONEL metal, but is preferably composed of tantalum or an alloy of tantalum which provides gamma-ray shielding. The shielding includes a central portion 275 of cylinders of foil of progressively increasing diameter from the capsule 233 outwardly and end portions 277 and 279 of generally frusto-conical form. The end portions 277 and 279 are composed of discs of approximate diameters. The foil may be dimpled like the foil of shield 101 and similarly positioned to minimize heat flow by conduction. The portion 279 encloses the thermoelectric element 235 and is formed of discs with coextensive holes forming an annular slot 281 through which the element 235 passes.

The thermoelectric element 235 includes a plurality of pairs of wires or rods 283. One wire of each pair is of one thermoelectric polarity, for example TOPHEL special alloy, and the other wire is of the opposite polarity, CUPRON special alloy. Each pair of wires 283 is secured by brazing to ceramic bushing 285 and 287, which are electrically insulating but have high thermal conductivity. The wires 283 of each pair are connected together in the bushings 285 at the hot junction 237, but are insulated from each other and extend out of the bushings 287 at the cold junction ends. The wire 283 of one polarity in each bushing 287 is joined to the wire of the opposite polarity of the next bushing 287.

The thermoelectric element 235 includes a cylindrical hot shoe 201 and a cylindrical cold shoe 293. The hot shoe 291 is bolted tightly to the disc 257 and the bushings 285 extend through holes in this shoe 291 and are in good heat-deriving relationship with this shoe 291. The bushings 287 pass through the cold shoe 293 and are in good heat-transfer relationship with this shoe 293. The hot shoe 291 is enclosed in a frusto-conical annular stack 279 of heat-radiation reflecting discs.

The above described assembly of heat capsule 233 and thermoelectric element 235 are enclosed in a resilient, generally cylindrical, cage-like enclosure 301 which compresses the element 235 into good heat transfer relationship with the capsule 233. The enclosure 301 is formed of strips 303 extending longitudinally of the assembly and of bases 305 and 307. Legs 309 and 311 respectively extend from each base 305 and 307. Tensioning spring rods 313 engage the strip 261 at one end and the legs 309 at the other, and pull the capsule 233 towards the base 305, compressing the heat shield portion 277. Tensioning spring rods 315 engage the legs 311 and the disc 257 and pull the hot plate 291 into good heat deriving relationship with the disc 257. The assembly of the thermoelectric element 235 and capsule 233 are cushioned against shock by resilient members 321 which are joined at one end to the plate 293 and the opposite end to the strips 303. The assembly is enclosed in a container 304, having a base 306 from which a box 308 extends. A feed through terminal 310 is sealed through the base 306.

One of the wires 283 is grounded to the cagelike member 301. This wire is connected through a wire 323 included in cable 325 to a lug 327 extending from a strip 303. The wire 283 of the opposite polarity, which passes through the next bushing 283, is connected to a wire 331 in a cable 333. The wire 331 passes through the feed through terminal 310 and thence the cable 333 passes through the box 308 where the cable is embedded in a potting compound such as SILICONE. The wire 333 is the negative hot terminal of the converter 231. The voltage between wires 333 and ground is equal to the sum of the voltages of the thermocouples in the annulus in series 235.

The converter 231, shown in FIGS. 12 and 13, is dimensioned for higher power output at the generator output than the generator shown in FIGS. 1 through 10. Typically, the converter shown in FIGS. 12 and 13 may serve to produce about 60 milliwatts of power at the generator output.

FIGS. 14 and 15 show a heat-to-electricity converter 341 similar to the converter shown in FIGS. 12 and 13, but with a flat rather than an annular thermoelectric element 343.

FIG. 16 shows another electrical converter which is used in the practice of this invention. The "hot" output terminal 69 or 333 is connected to the negative input terminal 351 of the converter. The positive terminal 353 is grounded. The multiwinding transformer T1 has a core 381 of SUPERMALLOY alloy. The 2305 transistors are connected in an oscillator circuit with windings S1 and S2. The 943 transistors are connected in a full wave rectifier circuit with winding S3. A DC potential is impressed on capacitors C30 and this supplies the load $R_L$. The 943 transistors are alternately driven to saturation by secondary S4.

Figure 17:
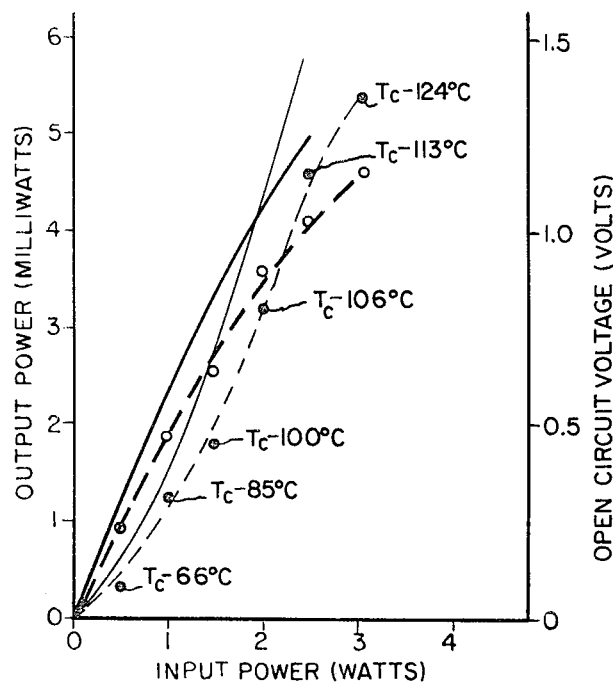
FIG. 17 is a graph composing the theoretically computed power output and voltage output as a function of input, actual power output and voltage output, of a heat-to-electricity converter in accordance with this invention.

FIG. 17 shows the actual and computed characteristics for a heat-to-electricity converter in accordance with this invention. In deriving the actual data, the heat power was supplied to the converter by an electric heater. Output power in milliwatts, and open-circuit output voltage in volts, are plotted vertically and input power in milliwatts horizontally. The light line curves are the curves for output power as a function of input, the broken line presenting actual measurement and the full line calculated output power. The heavy-line curves are the curves for output open-circuit voltage as a function of input power. The cold junction temperature Tc is indicated for the points of the actual power broken-line curve. It is noted that the cold-junction temperature increases substantially as the input power increases.

In the converter for which FIG. 17 was plotted, the heat-radiation shield was of tantalum, the tape was self-insulated and cold junction temperature Tc was not controlled.

Figure 18:
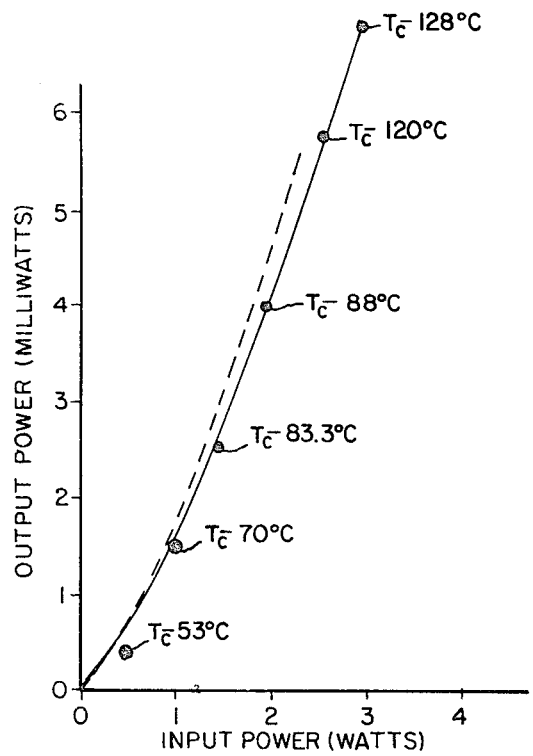
FIG. 18 is another graph similar to FIG. 17.

FIG. 18 is a graph similar to FIG. 2, but presenting only output power as a function of input power. The broken-line curve is the calculated curve and the full-line curve is plotted from data taken with an electric heater to supply the input power.

Figure 19:
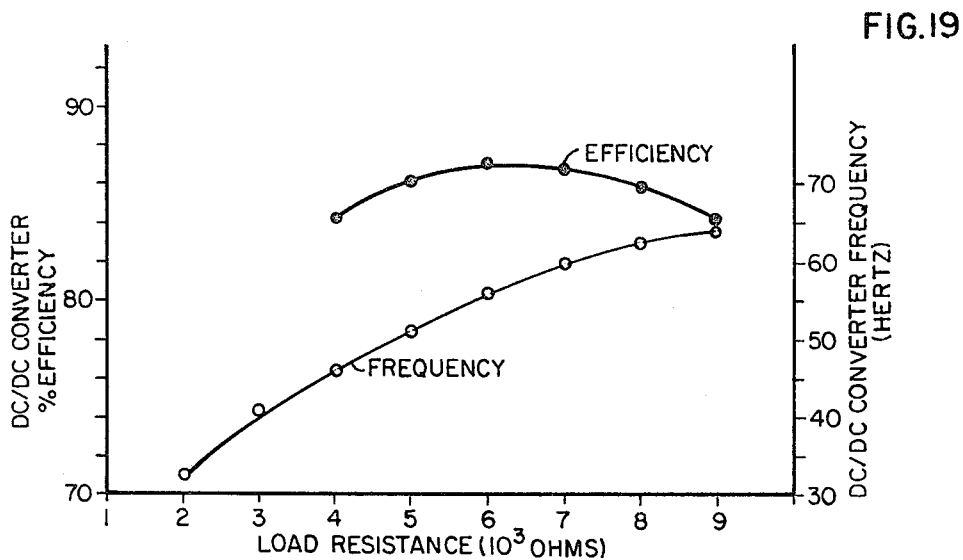
FIGS. 19 and 20 are graphs showing the operating characteristics of the solid-state converter shown in FIG. 16.

FIG. 19 is a graph showing the characteristics of a converter as shown in FIG. 16. Efficiency and converter frequency are plotted vertically and load resistance horizontally. It is noted that efficiency over a wide range exceeds 84% and is 87% for a load of 6000 ohms.

Figure 20:
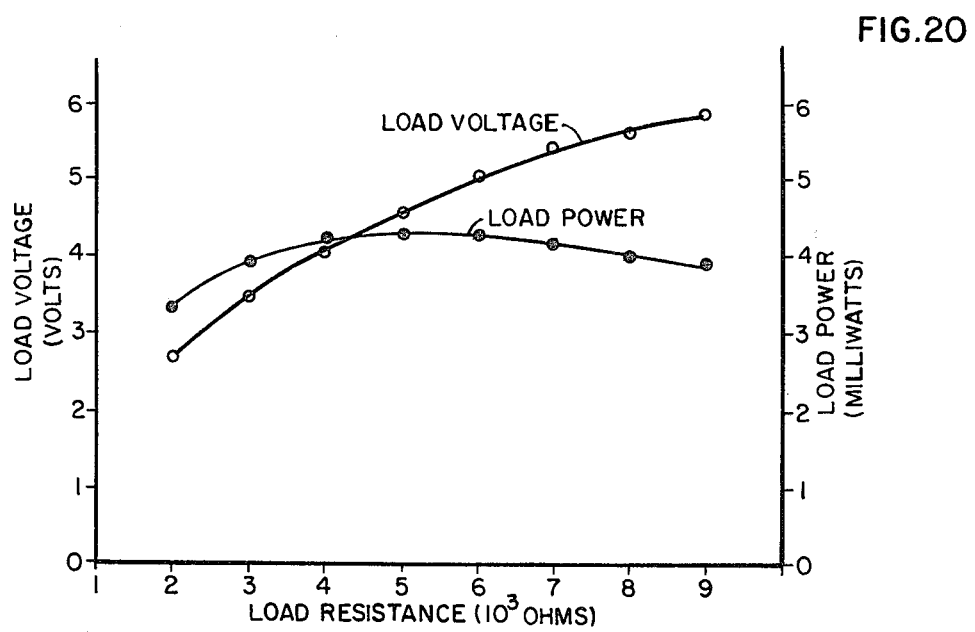

FIG. 20 is a graph for the converter shown in FIG. 16 in which load power and load voltage are plotted vertically and load resistance horizontally. The load power exceeds 4 milliwatts over the range from 3250 ohms to 8000 ohms.

Figure 21:
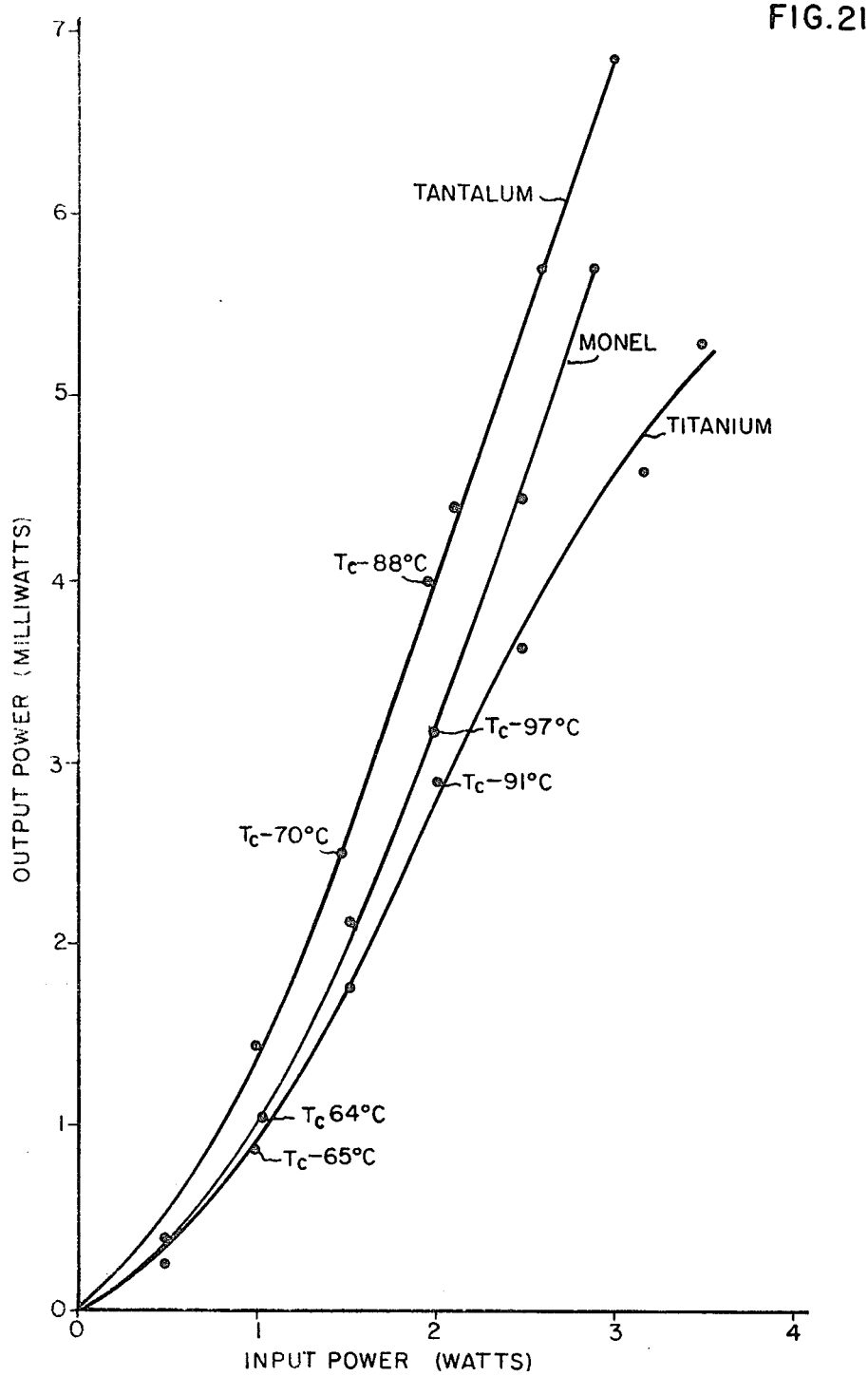
FIG. 21 is a graph comparing the effectiveness of titanium, MONEL alloy, and tantalum for heat-radiation shielding.

FIG. 21 shows the superiority of the tantalum as a heat-radiation shielding material. The data for these curves was derived for heat-to-electricity converters in which the heat power was supplied by an electric heater for all measurements. The center portion (103, FIG. 3; 275, FIG. 12) of the radiation shield was tantalum for all measurements. The end portions (105, 107, FIG. 3; 277, 279, FIG. 12) were titanium for one measurement, MONEL alloy for a second, and tantalum for the third.

For the three curves, output power is plotted vertically and input power horizontally. FIG. 21 shows that the tantalum provided the most effective shielding. The cold junction temperatures for the tantalum was substantially lower than Tc for the other shields at higher power outputs than for tantalum. And, the overall power output for the tantalum was substantially higher at the same power inputs. For example, at 2 watts input, the output for the titanium was 2.84 milliwatts, for MONEL 3.20 milliwatts, and for tantalum 4 milliwatts. The corresponding efficiencies are 0.143%, 0.160%, and 0.2%.

While preferred embodiments of this invention have been disclosed herein, many modifications are feasible. This invention then is not to be restricted, except insofar as is necessitated by the spirit of the prior art.

What is claimed is:

1. A heat-to-electricity converter including a heat source of radioactive material which produces gamma rays, a thermoelectric element having a hot junction and a cold junction; said hot junction being connected in heat deriving relationship with said source, a heat sink, said heat sink being connected in heat deriving relationship with said cold junction, and a multifoil shield substantially of tantalum foil interposed between said source and said cold junction for suppressing both heat radiation from said source to said cold junction and gamma rays, said thermoelectric element having a generally helical form such that any hypothetical radial line from the heat source to the heat sink intersects said thermoelectric element only once.

2. A heat-to-electricity converter including a container bounded by a thermally conducting wall and having disposed therein a heat source, a heat shield within said container enclosing said source, and a thermoelectric strip extending through said shield having a hot junction in heat-interchange relationship with said source and a cold junction in heat-interchange relationship with said wall, the only heat-conduction path through said strip from said hot junction to said cold junction being longitudinal of said strip, said source being generally cylindrical having a base and the thermoelectric strip having a generally helical form with the hot junction at inner end of the spiral and the cold junction at the outer end of the spiral, said hot junction end being in heat-exchange relationship with said source, the positioning of the strip in the container being such that any hypothetical radial line from the source to the wall intersects the strip only once, said source being radioactive, emitting gamma rays and the heat-shield is composed substantially of tantalum.

3. The converter of claim 2 wherein the source is generally cylindrical having a base and the thermoelectric strip is annular with the hot junction at one end of the annulus and the cold junction at the other end of the annulus, said hot junction end being in heat-exchange relationship with said base, the shield concentrating the heat energy of said source on said base.

4. The converter of claim 2 wherein the source is generally cylindrical having a base and the thermoelectric strip is in the form of a generally rectangular plate with the hot junction at one end and the cold junction at the opposite end, said hot junction end being in heat-exchange relationship with said base, the shield concentrating the heat energy of said source on said base.

5. A heat-to-electricity converter including a heat source, a heat sink, a tantalum foil shield interposed in heat-radiation-shielding relationship between said source and said sink, said shield enclosing said source and having therein a generally spiral cavity which winds around said source between said source and sink, in such a manner that any hypothetical radial line from the source to said heat sink intersects the cavity only once, and a thermoelectric element extending through said cavity from said source to said sink having a hot junction in heat-receiving relationship with said source and a cold junction in heat-transfer relationship with said sink.

* * * * *